United States Patent [19]

Salesses

[11] Patent Number: 5,138,125
[45] Date of Patent: Aug. 11, 1992

[54] ELECTRICAL NEEDLE DESTRUCTION DEVICE WITH STERILIZABLE ASSEMBLY

[76] Inventor: Richard V. Salesses, 3422 Lake Lesina Dr., San Jose, Calif. 95135

[21] Appl. No.: 439,304
[22] Filed: Nov. 21, 1989
[51] Int. Cl.⁵ .............................................. B23K 11/22
[52] U.S. Cl. ........................................ 219/68; 83/944
[58] Field of Search .............. 219/68; 128/919; 83/15, 83/16, 944

[56]  References Cited

U.S. PATENT DOCUMENTS

| | | | |
|---|---|---|---|
| 4,404,881 | 9/1983 | Hanifl | 83/944 |
| 4,565,311 | 1/1986 | Pugliese et al. | 83/944 |
| 4,628,169 | 12/1986 | Ch'ing-Lung | 219/68 |
| 4,877,934 | 10/1989 | Spinello | 219/68 |
| 4,915,698 | 4/1990 | Levenson | 128/919 |

Primary Examiner—Geoffrey S. Evans
Attorney, Agent, or Firm—Shlesinger, Arkwright & Garvey

[57]  ABSTRACT

A needle destruction device which prevents reuse of used needles and includes a pivotable removable and autoclavable needle receiver mounted on a receptacle. The receptacle contains a pair of electrodes through which current passes when a needle is placed across them and is destroyed. The receiver has a needle hub grasping plunger which grips the needle hub while the syringe is unscrewed therefrom. After separation of the needle hub from the syringe, the hub falls into a drawer inside the receptacle. The receiver is removable for serialization and is replaceable upon the receptacle.

20 Claims, 2 Drawing Sheets

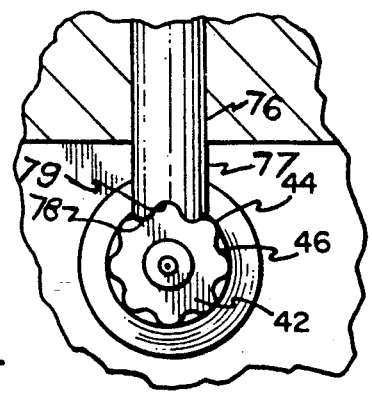
FIGURE 4
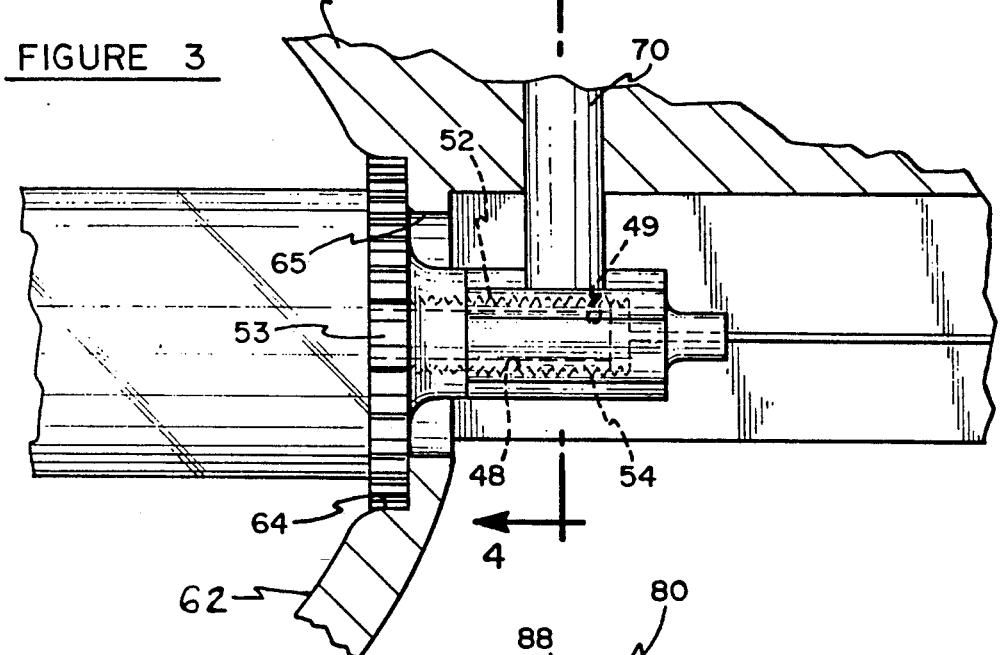
FIGURE 3
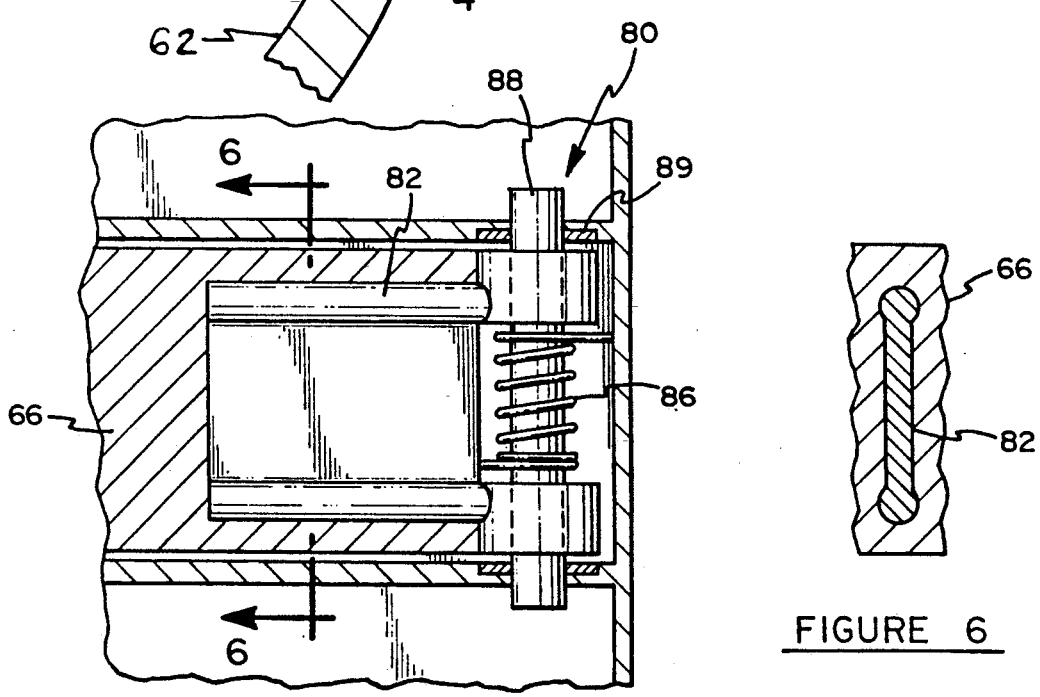
FIGURE 5
FIGURE 6

ND DESTRUCTION DEVICE# ELECTRICAL NEEDLE DESTRUCTION DEVICE WITH STERILIZABLE ASSEMBLY

FIELD OF THE INVENTION

This invention relates to the sanitary use and the destruction of used hypodermic needles, and particularly a device that both destroys a needle after use and permits it to be non-infectiously held because after prior use the needle handling parts can readily be disassembled and rendered non-infectious.

BACKGROUND OF THE INVENTION

In the medical/dental/medically related field, disposal of infectious waste has become a source of serious concern. No longer is the disposal problem only in regard to hospitals. As government regulations tighten, even small producers of hazardous medical/dental waste such as dentists and doctors offices must comply with stringent guidelines.

Of particular importance is the disposal of hypodermic needles used in administering medicines and taking body fluid samples. Many mechanical needle bending devices have been proposed which prevent needle reuse, and recent government guidelines discourage this practice, also the parts contacting the needle could not be sterilized. This had to be performed as an additional step.

One needle destruction device, U.S. Pat. No. 4,628,169 uses electric current to burn the needle to prevent its reuse. Some degree of sterilization may occur during electrical destruction of a portion of the needle. Furthermore, contamination of the syringe engaging the above device will occur. No provision is made for sterilization of the needle destruction device itself.

From the above, it can be seen that there is need for a small destructing device which combines sterilization via autoclaving with prevention of needle reuse. Consequently, it is desirable that such a device both quickly destroy used needles and is readily sterilizable.

SUMMARY OF THE INVENTION

Accordingly, a feature of this invention is a needle destruction device which provides for convenient needle holding and subsequent sterilization of the parts thereof which may possibly become themselves infected after contacting used hypodermic needles.

A still further feature of this invention is to provide a non-infectious needle holding device having parts which are readily disassembled and returned after use to a non-infectious condition via autoclaving to prevent cross-contamination of needles.

Yet another feature of the invention is that the needle and hub are completely sterilizable.

Yet another features of the invention is that the needle contacting parts of the destruction device is both sterilizable and reusable.

Still another feature of the invention is the use of electric current to destroy a needle quickly and efficiently without the need for the operator to hold it during the process.

In particular, this invention is directed to a needle and syringe receiver for a needle destruction device. The receiver part which supports and contacts the needle and syringe is detachably mounted to a housing containing a needle destruction means to permit sterilization. After insertion of a syringe containing a needle into the receiver, the needle can be separated from the syringe. After separation, the hub falls into the drawer of the receptacle. The drawer may be removed from the receptacle for sterilization and reuse.

These and other features and advantages of the invention will be readily apparent in view of the following description and drawings of the above-described invention.

BRIEF DESCRIPTION OF THE DRAWINGS

The above and other features and advantages of the present invention will become apparent from the following detailed description of the preferred embodiment of the invention illustrated in the accompanying drawings, wherein:

FIG. 3 is an enlarged fragmentary view of the syringe engaging portion of the receiver of the device shown in FIG. 2;

FIG. 4 is a cross-sectional view along line 4—4 of FIG. 3 showing the plunger engaging the needle hub;

FIG. 5 is an enlarged cross-sectional view of the receiver engaging tongue and pivoting hinge; and FIG. 6 is a cross-sectional view along line 6—6 of FIG. 5 showing the tongue inserted into a slot in the receiver arm.

DESCRIPTION OF THE INVENTION

Figure 1:
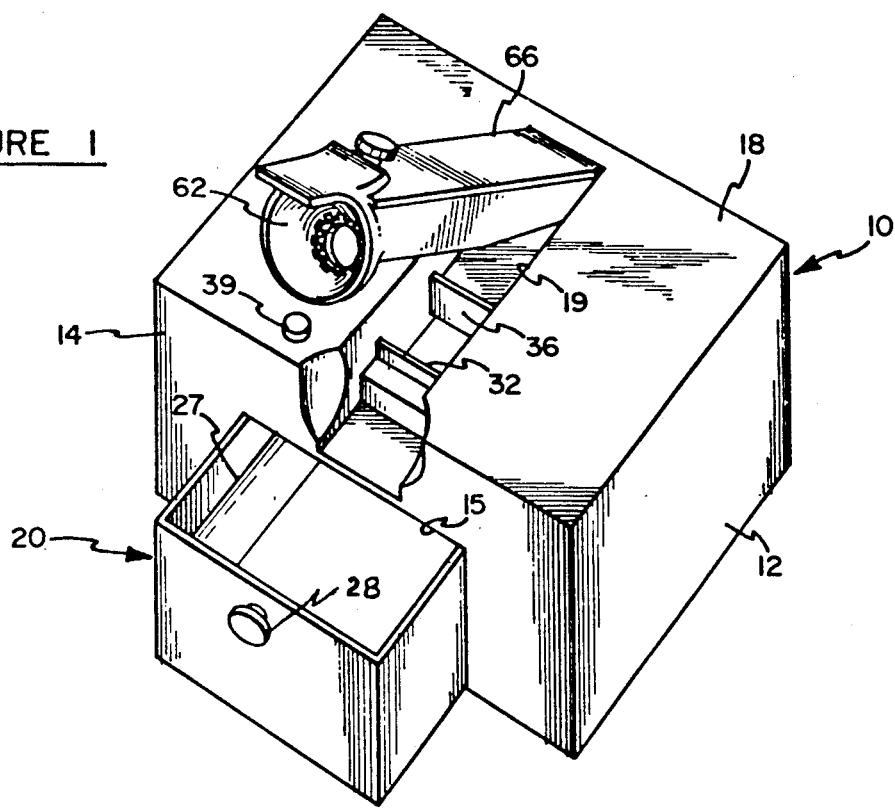
FIG. 1 is a perspective view of the needle destruction device.
Figure 2:
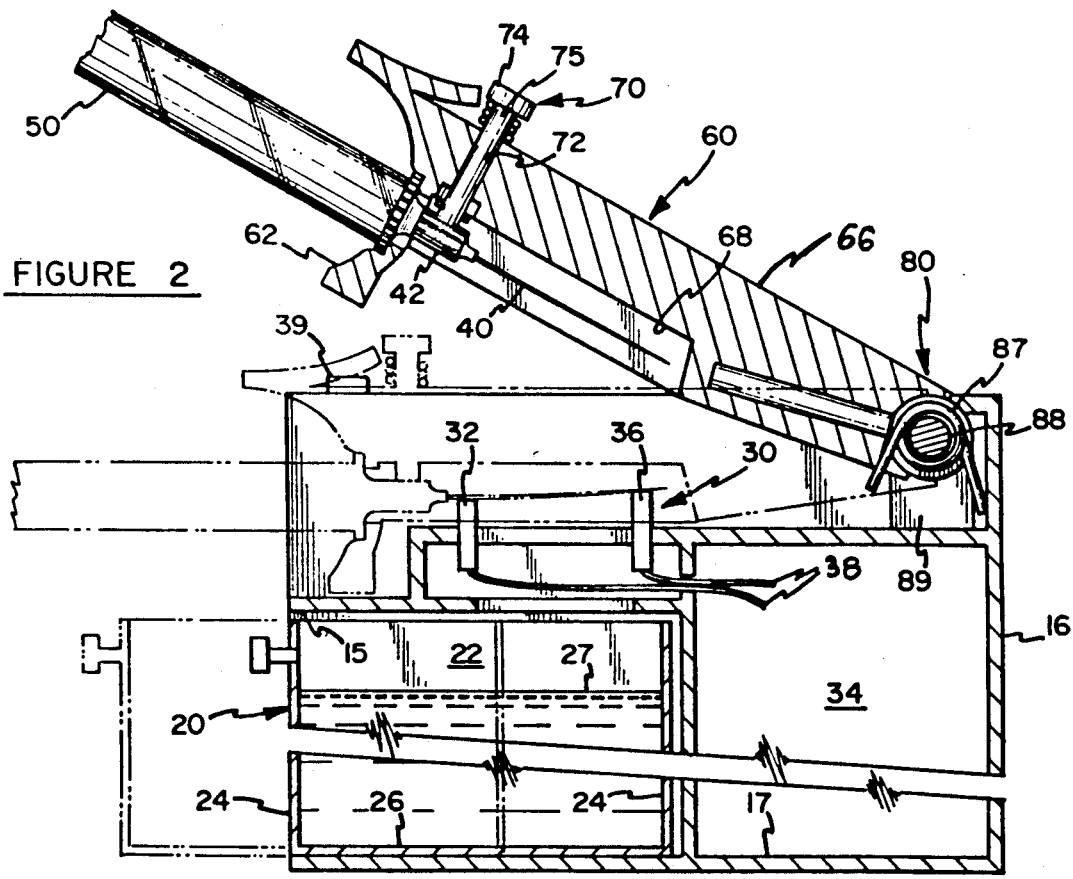
FIG. 2 is a side cross-sectional view in the receiving portion in operational position.

The needle destruction device as shown in FIGS. 1 and 2 includes a housing 10 having side walls 12, a front end wall 14, having a front opening 15, rear wall 16 and a top wall 18 having a top opening 19. A drawer 20 is located within housing 10 having sides 22, end panels 24, and a bottom wall 26. Normally, drawer 20 will contain a cold sterilizing solution 27. Drawer 20 includes a handle 28 for effecting inward and outward movement of the drawer 20 within the housing 10 through front opening 15. Drawer 20 is of a length between end panels 24 substantially less than the length of side walls 12.

The needle destruction apparatus 30 has a positive electrode 32 directly connected to a power source 34 and a negative electrode 36 which is grounded. Power is provided to positive electrode 32 by suitable power source 34 such as a battery contained within housing 10 or by connection to a transformer connected to a wall outlet (not shown). Positive electrode 32 and negative electrode 36 are connected to a conventional circuit (not shown). Suitable electrode leads 38 are connected to positive electrode 32 and negative electrode 36 to provide a complete electric circuit as indicated by the activation of light 39 when a needle 40 is placed across both positive electrode 32 and negative electrode 36. Preferably, power source 34 is of a rechargeable battery type which will provide current to the electrodes 32 and 36 to provide current through the needle 40. The amperage used will determine the speed of needle destruction.

Needle 40 is part of a knurled needle hub 42 and extends therethrough as best shown in FIGS. 3 and 4. Knurled hub 42 has thereon a series of ridges 44 and valleys 46. Knurled hub 42 includes female threads 48 on its hollow interior 49.

Syringe body 50 is of somewhat larger diameter than knurled needle hub 42. A fitting 52 is provided at the dispensing end 54 of syringe body 50. Fitting 52 has male threads provided thereon for threadable complementary engagement with female threads 48 of knurled needle hub 42 as shown in FIG. 3.

Needle receiver assembly 60 as best shown in FIGS. 2 and 3, includes a funnel-shaped portion 62 having an opening 64 therein for reception and holding of needle 40 and knurled needle hub 42. It is made of autoclavable material, i.e., material that has a sufficiently high melting point to withstand exposure to heat or sterilizing chemicals during the time that it is held in the sterilizer or autoclave unit. It is possible to use different types of noncorrosive metals such as stainless steel, and high melting point plastics. The diameter of opening 64 is slightly less than the diameter of syringe body 50, such that syringe body 50 will not pass through opening 64, but rest against stop 65. Preferably, needle receiver assembly 60 is constructed of PFA TEFLON, but stainless steel and other plastics may be used. PFA TEFLON is preferred for its chemical resistance properties and is usable throughout a wide temperature range.

Needle receiver assembly 60 includes a support arm 66 extending from funnel-shaped portion 62. An open channel 68 is formed in support arm 66 to provide a passageway for needle 40 and knurled needle hub 42 when they are inserted into opening 64. Channel 68 is slightly longer than needle 40.

Plunger 70 extends through support arm 66 just behind funnel-shaped portion 62. Plunger 70 is an elongated rod which is a movable spring tension rod through passageway 72 formed in support arm 66. Plunger 70 further includes a head 74 having a shoulder 75 which prevents plunger 70 from slipping through passageway 72. Plunger bottom 76 has a foot 77 having ridges 78 and a valley 79 which correspond to ridges 44 and valleys 46 of knurled needle hub 42. Plunger 70 provides a friction grip on knurled needle hub 42, when separation of syringe body from knurled needle hub 42 is desired. Removal of knurled needle hub 42 from syringe body 50 is accomplished by applying downward pressure with thumb on funnel-shaped portion 62 and downward finger pressure to plunger 70 which frictionally grips and prevents rotation of knurled needle hub 42 as syringe body 50 is rotated by hand.

Needle receiver assembly 60 is pivotally connected to housing 10 by hinge 80. Hinge 80 includes a projecting tongue portion 82 which is engageable with support arm 66 by slidable insertion into complementarily shaped slot 84. The slidable engagement of tongue portion 82 with slot 84 allows removability and replacement of needle receiver assembly 60. Hinge 80 is securely mounted to housing 10 and is biased in the upward sloping direction by spring 86. Hinge 80 is pivotable through the movement of sleeve 87 around pin 88. Pin 88 connects sleeve 87 to housing 10 by ears 89 which are connected to top wall 18 of housing 10.

OPERATION

A needle 40 can be destructed by a needle destruction device herein described by insertion of a syringe body 50 containing a needle 40 and knurled needle hub 42 into the needle receiver assembly 60 through opening 64 in funnel-shaped portion 62. When fully inserted needle 40 extends into open channel 68. The knurled disc portion 53 of fitting 52 is set into and frictionally retained by the periphery of the opening 64 so that the needle and syringe can be independently supported without manual support clear of the needle destruction means.

To activate the needle destruction apparatus 30, needle receiver assembly 60 is pivoted downwardly by thumb pressure on funnel-shaped portion 62 from an inclined first holding position until the needle is to be destroyed. Then it is moved to a nearly horizontal second needle destruction position where needle 40 engages positive electrode 32 and negative electrode 36. Preferably, negative electrode 36 extends slightly higher upwardly than positive electrode 32, to ensure that needle 40 is grounded prior to contact with positive electrode 32.

Contact of needle 40 with positive electrode 32 and negative electrode 36 completes an electric circuit and electric current flows through needle 40 and causes needle 40 to be destroyed. Light 39 is illuminated during current flow through the needle while the circuit is complete. Upon needle destruction, the current flow stops and light 39 goes out indicating that the needle destruction process is complete.

After destruction of needle 40, continued thumb pressure is applied to knurled needle hub 42 through plunger 70. The operator of the device presses a finger on plunger head 74 to engage foot 77 on knurled needle hub 42. While plunger 70 prevents rotation of knurled needle hub 42, syringe 50 is unscrewed and separated from knurled needle hub 42. Upon separation, knurled needle hub 42 drops into drawer 20. As previously noted, drawer 20 can contain a cold sterilizing solution 27 which sanitizes knurled needle hub 42 and any residual remains of needle 40. Drawer 20 is a removable autoclavable part of the device that ensures that its remaining contents can be rendered non-infectious.

After syringe body 5 has been removed from needle receiver assembly 60, assembly 60 may be separated from housing 10 by sliding support arm 66 off tongue portion 82. Needle receiver assembly 60 may then be sterilized by autoclaving.

While this invention has been described as having a preferred embodiment, it is to be understood that the invention is capable of further modification, uses or adaptations which follow in general the principle of the invention and includes such departures from the present disclosure as come within known or customary practice in the art to which the invention pertains, and fall within the scope of the appended claims.

What is claimed is:

1. A syringe holding and needle destruction device for disposing of hypodermic syringe needles and to prevent cross-contamination comprising:
   a) a housing having an opening therein for receiving a used hypodermic needle,
   b) needle destruction means disposed within the housing adjacent the opening for contacting and destroying the needle to prevent reuse thereof,
   c) syringe and hypodermic needle receiving and supporting means mounted on the housing adjacent the opening for receiving the needle and supporting the syringe until the needle is to be destroyed by engagement with the needle destruction means,
   d) at least a portion of said syringe and hypodermic needle receiving and supporting means being removably mounted, and,
   e) whereby, said portion can be made non-infectious to prevent cross-contamination and thereafter remounted for reuse.

2. The syringe holding and needle destruction device for disposing of needles in a non-infectious manner as set forth in claim 1, wherein:
   a) said needle receiving means is pivotable relative to said housing when said receiving means is attached to said housing.

3. The syringe holding and needle destruction device for disposing of needles in a non-infectious manner as set forth in claim 2, wherein:
   a) said housing includes hinge means having attachment means for detachable attachment of said needle receiving means.

4. The syringe holding and needle destruction device for disposing of needles in a non-infectious manner as set forth in claim 2, wherein:
   a) said needle receiving means is constructed of autoclavable material for sterilization and is reusable.

5. The syringe holding and needle destruction device for disposing of needles in a non-infectious manner as set forth in claim 1, wherein:
   a) said needle receiving means is moveable from a first position wherein a needle inserted therein does not contact said needle destruction means, to a second position wherein a needle inserted therein contacts said needle destruction means.

6. The syringe holding and needle destruction device for disposing of needles in a non-infectious manner as set forth in claim 5, wherein:
   a) said first position is generally inclined, and
   b) said second position is generally horizontal.

7. The syringe holding and needle destruction device for disposing of needles in a non-infectious manner as set forth in claim 1, wherein:
   a) said needle destruction means includes a pair of spaced apart electrodes, and
   b) said electrodes being positioned in said housing so that a needle supported by said needle receiving means may be moved into contact with said electrodes and be destroyed.

8. A needle destruction device for use with a needle and syringe assembly wherein the needle has a threaded hub attached thereto for threadable connection to a syringe, comprising:
   a) needle holding means for independently holding and supporting a needle and a syringe,
   b) needle destruction means for preventing reuse of a needle, and
   c) said needle holding means further including hub gripping means for preventing rotation of a needle hub when a syringe is unscrewed therefrom,
   d) said needle destruction means being positioned relative to said needle holding means so that a needle held by said needle holding means may be brought into contact with and rendered unusable by said needle destruction means.

9. The needle destruction device for use with a needle and syringe assembly as set forth in claim 8, wherein:
   a) said needle holding means is reusable after being rendered non-infectious.

10. The needle destruction device for use with a needle and syringe assembly as set forth in claim 9, wherein:
    a) said needle holding means is constructed of autoclavable material.

11. The needle destruction device for use with a needle and syringe assembly as set forth in claim 8, wherein:
    a) said needle destruction device further includes a receptacle, and
    b) said needle holding means is detachably attachable to said receptacle.

12. The needle destruction device for use with a needle and syringe assembly as set forth in claim 11, wherein:
    a) said receptacle houses said needle destruction means.

13. The needle destruction device for, use with a needle and syringe assembly as set forth in claim 12, wherein:
    a) said needle destruction means includes a pair of spaced apart electrodes connected to an electrical circuit, and
    b) whereby, a needle may be rendered unusable when placed across both electrodes and current flows between said electrodes through the needle.

14. The needle destruction device for use with a needle and syringe assembly as set forth in claim 13, wherein:
    a) said needle destruction means is powered by a battery.

15. The needle destruction device for use with a needle and syringe assembly as set forth in claim 14, wherein:
    a) said battery is rechargeable.

16. A needle destruction device, comprising:
    a) a housing which contains a needle destruction assembly,
    b) needle and syringe receiving means for receiving and supporting a needle and syringe,
    c) said needle receiving means and said needle destruction assembly being moveable relative to each other from a separated first holding position to a second needle destruction position,
    d) the first position being such that a needle may be safely inserted in said needle receiving means independently supported clear of the needle destruction assembly and held for possible reuse until it is to be destroyed and the second position being such that a needle held by said needle receiving means is moved into contact with said needle destruction assembly and is destroyed, and,
    e) at least a part of the removable needle and syringe receiving means being removable, reusable, and made of material which will permit it to be placed in an autoclave.

17. The needle destruction device as set forth in claim 16, wherein:
    a) said needle destruction means is electrically operated.

18. A syringe holding and needle destruction device for disposing of hypodermic syringe needles and to prevent cross-contamination, comprising:
    a) needle and syringe receiving means for receiving and supporting a needle syringe in an accessible position for possible reuse until it is to be destroyed,
    b) needle destruction means for destroying a needle which is closely and operatively associated with the needle and syringe receiving means for destroying needles,
    c) at least a portion of said syringe needle receiving means being removable and made of material to permit it to be autoclaved to preclude cross contamination.

19. The syringe holding and needle destruction device as set forth in claim 18, wherein:

a) the receiving means has a funnel-shaped configuration which has an opening therethrough for receiving the syringe and needle in an independently supported position clear of the needle destruction means.

20. The syringe holding and needle destruction device as set forth in claim 18, wherein:

a) locking means is associated with the needle and syringe receiving means for holding the syringe and needle in position.

* * * * *